US012594183B2

(12) United States Patent
Nguyen

(10) Patent No.: US 12,594,183 B2
(45) Date of Patent: Apr. 7, 2026

(54) MOUTHGUARD

(71) Applicant: PEACEFULSLEEP PTY LTD, Maribyrnong (AU)

(72) Inventor: Hoang Nguyen, Reservoir (AU)

(73) Assignee: PEACEFULSLEEP PTY LTD, Maribyrnong (AU)

( * ) Notice: Subject to any disclaimer, the term of this patent is extended or adjusted under 35 U.S.C. 154(b) by 281 days.

(21) Appl. No.: 18/011,697

(22) PCT Filed: Jun. 16, 2021

(86) PCT No.: PCT/AU2021/050620
§ 371 (c)(1),
(2) Date: Dec. 20, 2022

(87) PCT Pub. No.: WO2021/258129
PCT Pub. Date: Dec. 30, 2021

(65) Prior Publication Data
US 2023/0225899 A1     Jul. 20, 2023

(30) Foreign Application Priority Data

Jun. 24, 2020     (AU) ................................. 2020902101

(51) Int. Cl.
A61F 5/56         (2006.01)
(52) U.S. Cl.
CPC ........ A61F 5/566 (2013.01); *A61F 2005/563* (2013.01)
(58) Field of Classification Search
CPC ............. A61F 5/56–566; A63B 71/085; A63B 2071/086; A63B 2071/088; A61C 7/08; A61C 7/36
See application file for complete search history.

(56) References Cited

U.S. PATENT DOCUMENTS

| | | | |
|---|---|---|---|
| 5,003,994 A * | 4/1991 | Cook ...................... | A61F 5/566 |
| | | | 128/859 |
| 5,092,346 A | 3/1992 | Hays et al. | |
| 5,868,138 A * | 2/1999 | Halstrom ................ | A61F 5/566 |
| | | | 128/859 |
| 6,055,986 A | 5/2000 | Meade | |
| 6,895,970 B1 | 5/2005 | Lawrence et al. | |
| 2011/0162658 A1 | 7/2011 | Fisher et al. | |
| 2014/0130807 A1 | 5/2014 | Hart | |

OTHER PUBLICATIONS

International Search Report and Written Opinion for PCT/AU2021/050620, mailed Aug. 30, 2021.

* cited by examiner

*Primary Examiner* — Michelle J Lee
(74) *Attorney, Agent, or Firm* — Pilloff Passino & Cosenza LLP; Rachel K. Pilloff; Sean A. Passino

(57)          ABSTRACT

A mouthguard for protecting a wearer's teeth from bruxism, the mouthguard comprising: (a) a cavity configured to receive at least a portion of a first row of teeth of the wearer; (b) a guide extending towards the wearer's second row of teeth, the guide being configured to guide the jaw of the second row of teeth such that in use, when the wearer brings their teeth together, front teeth of the opposed jaws are brought substantially into alignment with one another; and (c) a bite region at a base of the guide configured, in use, to abut the front teeth of the second row of teeth when the wearer brings their teeth together.

6 Claims, 4 Drawing Sheets

Figure 1

MOUTHGUARD

TECHNICAL FILED

The present invention relates to a mouthguard for protecting against bruxism. In embodiments of the invention, the mouthguard may also address or reduce the severity of other issues, such as temporomandibular joint dysfunction and snoring.

BACKGROUND

Bruxism refers to the grinding of teeth, often involuntarily and typically during sleep. It can be an unconscious behaviour wherein a person clenches their jaws together and slides their top and bottom teeth back and forth over each other. This grinding of the teeth can cause muscular pain, joint dysfunctions, headaches, damage to the teeth, among other problems. Mouthguards have been developed in attempts to address problems posed by teeth grinding.

However, existing over-the-counter mouthguards are often ill-fitting, whereas customised mouthguards require the services and expenses associated with a dentist or other skilled technicians or practitioners. In addition to cost, they are typically quite bulky and can compromise one's ability to speak or breathe, the latter being of particular importance during sleep, especially if one is prone to snoring or suffers from sleep apnoea. Additionally, if one is prone to snoring, they may already wear oral inserts which attempt to combat snoring but do not alleviate problems associated with bruxism.

Existing mouthguards simply allow a wearer to bite and grind against the mouthguard, rather than against their own teeth. Existing mouthguards do not manipulate or substantially alter the position of the wearer's jaw(s), and as such, while the wearer may not make direct teeth-on-teeth contact, the wearer is still able to tightly clench their jaws together, and this can result in headaches and long-term muscle pain and joint dysfunctions. Additionally, since the wearer is still grinding against the mouthguard (as opposed to their own teeth), these mouthguards may eventually be worn down and need to be replaced.

There is a need to address the above, and/or at least provide a useful alternative.

SUMMARY

According to a first aspect of the present invention, there is provided a mouthguard for protecting a wearer's teeth from bruxism, the mouthguard comprising:

(a) a cavity configured to receive at least a portion of a first row of teeth of the wearer;

(b) a guide extending towards the wearer's second row of teeth, the guide being configured to guide the jaw of the second row of teeth such that in use, when the wearer brings their teeth together, front teeth of the opposed jaws are brought substantially into alignment with one another; and (c) a bite region at a base of the guide configured, in use, to abut the front teeth of the second row of teeth when the wearer brings their teeth together.

In embodiments of the mouthguard, the bite region is spaced from the cavity such that in use, when the wearer bites against the bite region, the bite region maintains the front teeth of the opposed jaws at a distance from one another.

In embodiments of the mouthguard, the mouthguard is configured to be worn at least partially over a wearer's top row of teeth, the guide comprising a ramped surface which extends rearwardly and downwardly towards the wearer's bottom row of teeth such that, in use, as the wearer attempts to bring their rows of teeth together, front teeth of the wearer's bottom row of teeth contact a lower end of the guide and are guided forward so as to be substantially aligned and spaced apart from the front teeth of the wearer's top row of teeth.

In embodiments of the mouthguard, the guide comprises an opening through which air can flow.

In embodiments of the mouthguard, the mouthguard comprises an exterior shell portion and a mouldable interior portion securable thereto, which mouldable interior comprises said cavity configured to mould to the wearer's teeth.

In embodiments of the mouthguard, the bite region comprises:

(a) an at least partially hollow step disposed between the cavity and the guide, which step comprises one or more openings; and (b) a generally pliable foot extending downwardly from the interior portion and being insertable into the hollow step and exudable through the one or more openings of the step so as to define a surface of the bite region for abutment against the wearer's teeth.

In embodiments of the mouthguard, the mouthguard further comprises one or more grooves or ridges configured to locate the wearer's teeth in the mouthguard.

BRIEF DESCRIPTION OF THE DRAWINGS

An embodiment of the invention will now be described, by way of example only, with reference to the accompanying drawings in which:

FIG. 1 is a side perspective view of a mouthguard according to embodiments of the invention;

FIG. 2(*b*) is a front perspective view of an outer component of the mouthguard of FIG. 1;

FIG. 3(*b*) is a bottom view of the inner component of FIG. 2(*a*);

FIG. 4(*b*) is a side view of the mouthguard of FIG. 1; and

FIG. 4(*c*) is a front view of the mouthguard of FIG. 1.

DETAILED DESCRIPTION

Figure 1:
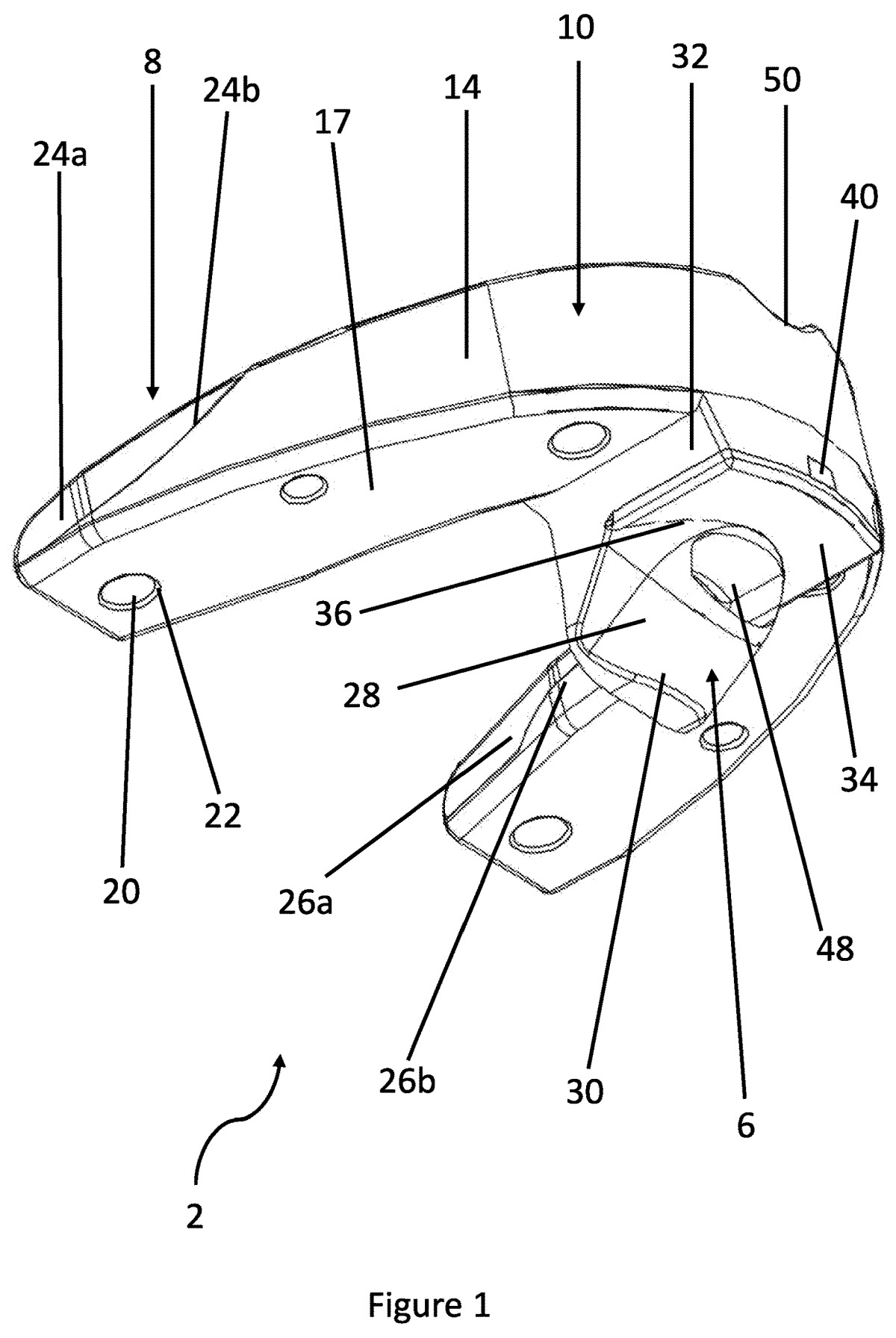

A mouthguard 2 according to embodiments of the invention is shown in FIG. 1. The mouthguard 2 is configured to protect a wearer's teeth from bruxism. In the depicted embodiment, the mouthguard 2 is configured to fit a wearer's top row of teeth and comprises a downwardly extending guide 6 providing a sloped surface that guides the wearer's lower jaw to a position wherein the front teeth of both jaws are substantially aligned and spaced from one another. In particular, compared with the position a person's lower jaw would be in if they naturally closed their mouth and brought their teeth together when a user attempts to bring their teeth together while wearing the mouthguard 2, the lower jaw is guided downwards and forwards so that the front teeth thereof are substantially aligned but spaced from the front teeth of the upper jaw. This positioning of the wearer's lower jaw may help combat bruxism and issues stemming therefrom and may help to reduce or even eliminate snoring and/or temporomandibular joint dysfunction (TMD).

Figure 2A:
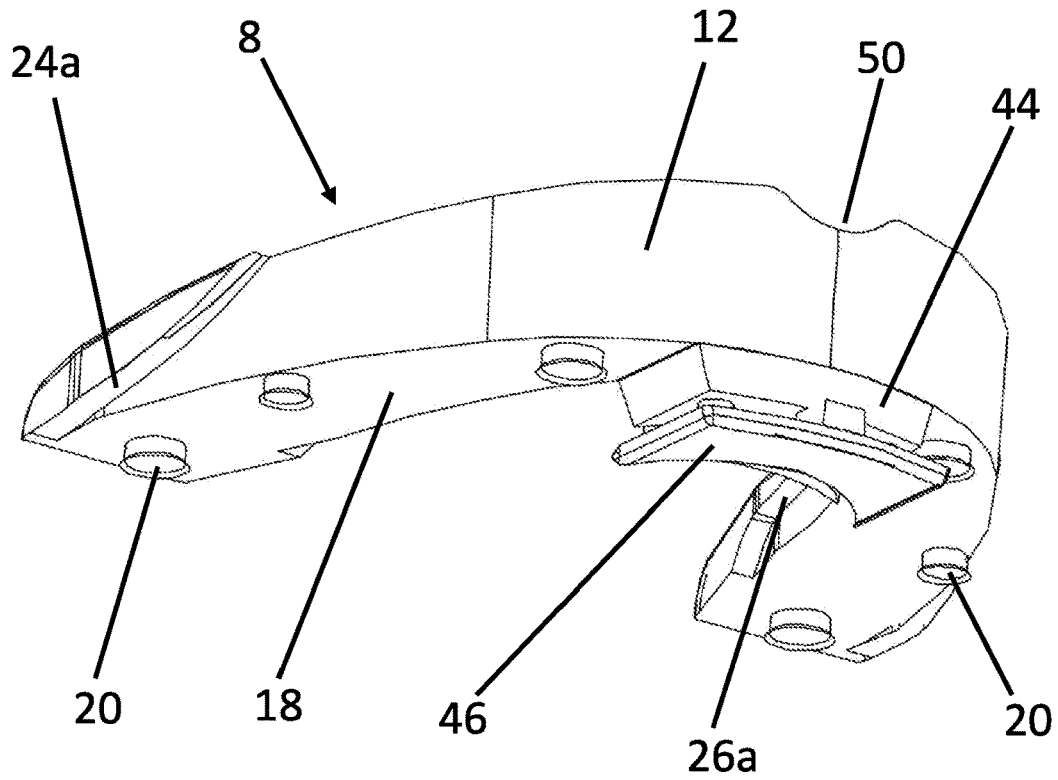
FIG. 2(*a*) is a front perspective view of an inner component of the mouthguard of FIG. 1.
Figure 2B:
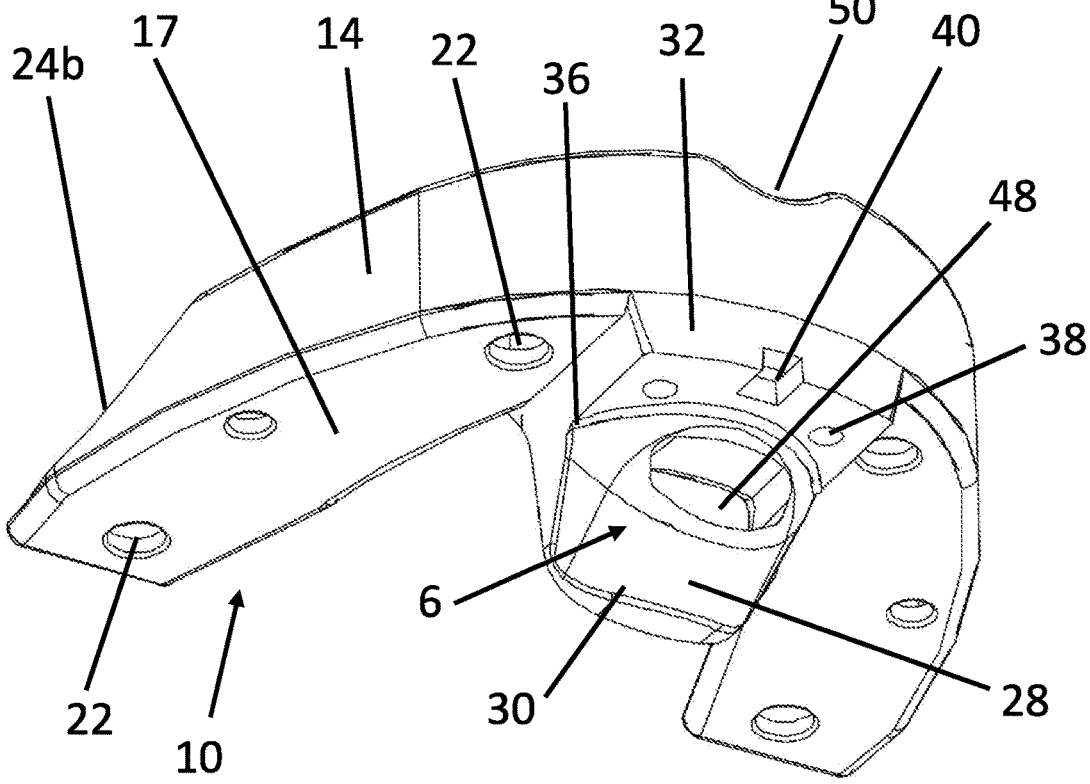
Figure 3B:
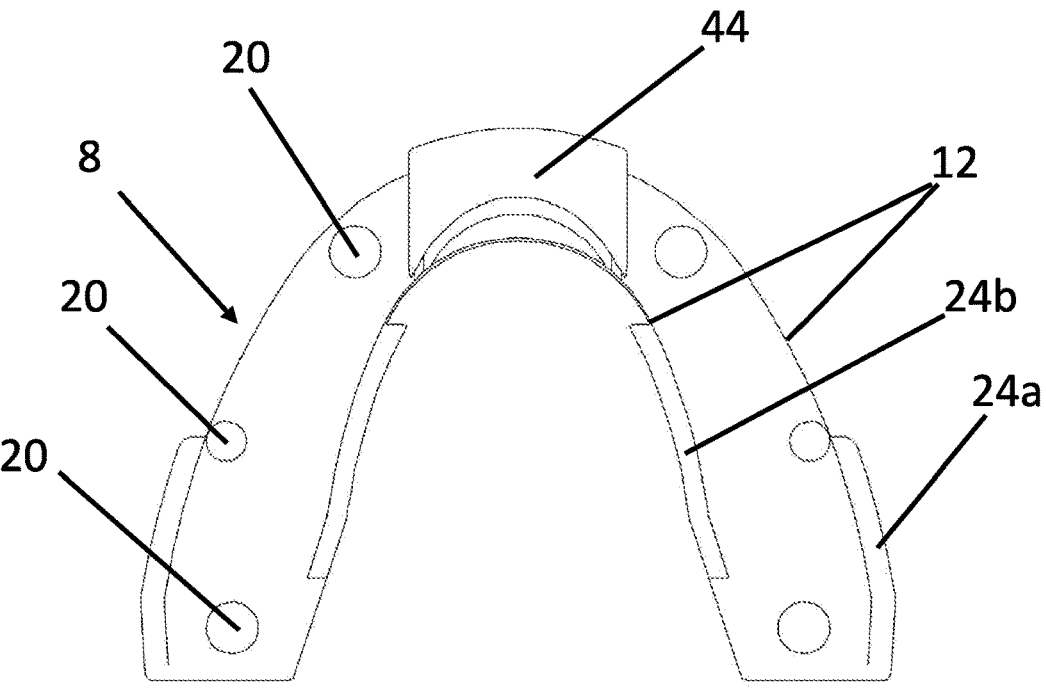
Figure 4A:
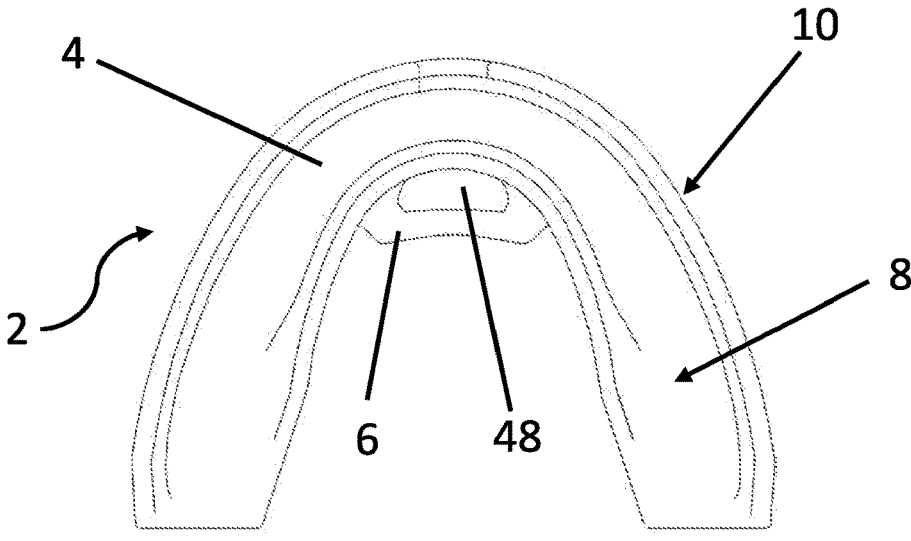
FIG. 4(*a*) is a top view of the mouthguard of FIG. 1.

In preferred embodiments of the invention, the mouthguard 2 is formed from two components 8, 10 each of which is shown in FIGS. 2(a) and 2(b), respectively. FIG. 2(a) shows a first or inner component 8 of the mouthguard 2. The inner component 8 comprises a surface for receiving the wearer's teeth. In the depicted embodiment, the surface is part of a U-shaped channel 4 (see FIG. 4(a)) formed by curved and opposed side walls 12 (see FIG. 3(b)) interconnected by a lower planar wall 18.

From a cross-sectional view, the channel 4 is generally U-shaped. From a plan view, the inner component 8 is also generally U-shaped. Of course, the surface which ultimately receives the teeth may not need to be part of a U-shaped channel 4. For example, the inner component 8 might have more of an L or hook-shaped cross-section, in which case the surface upon which the teeth bites can be defined by the shorter edge of the L or hook-shaped cross-section.

At least a portion, if not a substantial portion, of the inner component 8 (particularly the channel section 4 which receives the wearer's teeth) may be formed from a mouldable putty-like material. For example, the mouldable material could be thermoplastic EVA (ethylene vinyl acetate). The inner component 8 can thus be shaped to conform to a wearer's top teeth and/or gums. For example, the inner component 8 could be submerged in warm or hot water to allow the inner component 8 to be mouldable, whereupon the wearer can bite into the channel 4 of the inner component 8, gently pressing it against their top teeth such that as the inner component 8 cools and hardens, it retains a mould of the user's top teeth and/or gums.

The second or outer component 10 of the mouthguard 2 comprises a relatively rigid outer shell 10, as depicted in FIG. 2(b). It also comprises a U-shaped channel 14 (see FIG. 3(a)) formed by curved and opposing side walls 16 interconnected by a lower planar wall 17. The channel 14 of the outer component 10 is configured to receive the inner component 8 of FIG. 2(a). In the depicted example, the inner component of FIG. 2(a) may be lowered down and inserted into the outer shell component 10 of FIG. 2(b).

Each component 8, 10 may be provided with interlocking features which enable the inner mouldable component 8 to remain secured to the outer shell component 10. For example, in the Figures, a lower planar surface 18 of the U-shaped channel 4 of the inner component 8 is provided with resilient projections 20; the interior of the channel 14 of the outer shell component 10 is provided with complementary through holes 22 configured to receive respective projections 20 of the inner component 8. The complementary projections 20 and recesses 22 thus enable a secure mechanical interlocking between the inner component 8 and the outer component 10 of the mouthguard 2.

The projections 20 may take on any suitable shape to enable an interlocking between the two components 8, 10. For example, the projections 20 may be cylindrical, rectangular, and/or have a lower outward tapering. The complementary through holes 22 may form an interference fit with the projections 20.

Of course, other forms of securing the two components 8, 10 are within the scope of the present patent specification. For example, an adhesive may be applied to stick the two components 8, 10 together. Alternatively, a system of complementary grooves and ridges may also allow the two components 8, 10 to engage with one another.

The two components 8, 10 of the mouthguard 2 may also have additional features which help guide and secure their engagement with one another. In the depicted embodiment, the inner and outer sides of each of the posterior arms of the U-shaped channels 4, 14 may comprise complementary ramped surfaces 24a, 24b, 26a, 26b configured to engage one another. For example, referring to FIG. 2(a), the outer side of the posterior end of the first component 8 comprises a ramped surface 24a; referring to FIG. 2(b), the outside side of the posterior end of the second component 10 comprises a complementary ramped surface 24b configured to engage ramped surface 24a, as shown in FIG. 1. Similarly, the inner side of the posterior end of the first component 8 comprises a ramped surface 26a configured to engage a complementary ramped surface 26b at an inner side of the posterior end of the second component 10 (see FIGS. 1, 2(a) and 3(a)).

In certain embodiments of the mouthguard 2, the two components 8, 10 may be configured so they are not separable from one another. However, in other embodiments, the mouthguard 2 can be configured such that the two components 8, 10 are separable from one another, which can be beneficial if the wearer wants to alter certain characteristics of their mouthguard 2. For example, they may wish to use a shell 10 with a certain colour or design, or perhaps they may wish to use an inner component 8 associated with a certain flavour.

The inner mouldable component 8 serves to allow the mouthguard 2 to fit comfortably to a wearer's teeth. The inner component 8 sits securely within the outer shell component 10, which itself helps to protect against bruxism. In particular, when worn (during sleep for example), the mouthguard 2 guides a wearer's lower jaw downwards and forwards so that the wearer's four frontmost teeth are substantially aligned with one another, as will henceforth be described.

The outer shell component 10 comprises a guide 6 for guiding the wearer's lower jaw. The guide 6 comprises a downwardly extending projecting member which slopes rearwardly from the perspective of the wearer. The guide 6 provides a ramped surface 28 which helps bring a wearer's lower jaw downwards and forwards as the wearer brings their teeth together. In particular, when a wearer's rows of teeth are separated, grinding does not occur, but as they close their mouth and bring their lower teeth towards their upper teeth, the frontmost teeth of the lower jaw will first make contact with a lower end and/or outer face 30 of the guide 6. As the wearer continues closing their mouth and moving their teeth along the curved face 28 of the guide 6, the ramped surface 28 guides their lower front teeth, and thus the lower jaw, downwards and forwards. As such, even if the wearer moves their jaw to try and clench their teeth together, the mouthguard 2 acts to bring the lower jaw downwards and forwards such that the front teeth thereof are substantially aligned with the front teeth of the upper jaw. In this position, the mouthguard impedes or prevents the closing muscles of mastication from excessive muscle contraction, thereby reducing the likelihood of bruxism-induced headaches, TMD and other related issues.

In the depicted embodiment, the guide 6 has a curved profile that is configured to conform with the curved arrangement of the wearer's lower front teeth. As such, as the wearer closes their mouth, the curved profile of the guide 6 also helps centre the wearer's lower jaw.

To assist with keeping the wearer's jaw downwards, the mouthguard 2 may be provided with a raised and biteable surface, platform or step 32 which extends downwardly from a central front region of the outer shell component 10. As such, even when a wearer attempts to bite their teeth together, in addition to the guide 6 bringing their lower jaw forwards, the platform 32 keeps the wearer's front teeth from each jaw at a distance from one another, thereby retaining the wearer's lower jaw in a lowered position. This has the advantage of helping to better open the wearer's airway, thereby reducing, or eliminating their inclination to snore. This repositioning of the jaw also helps to bring the wearer's tongue downwards and forwards, which can help to keep the wearer's airway open and reduce snoring.

Figure 4B:
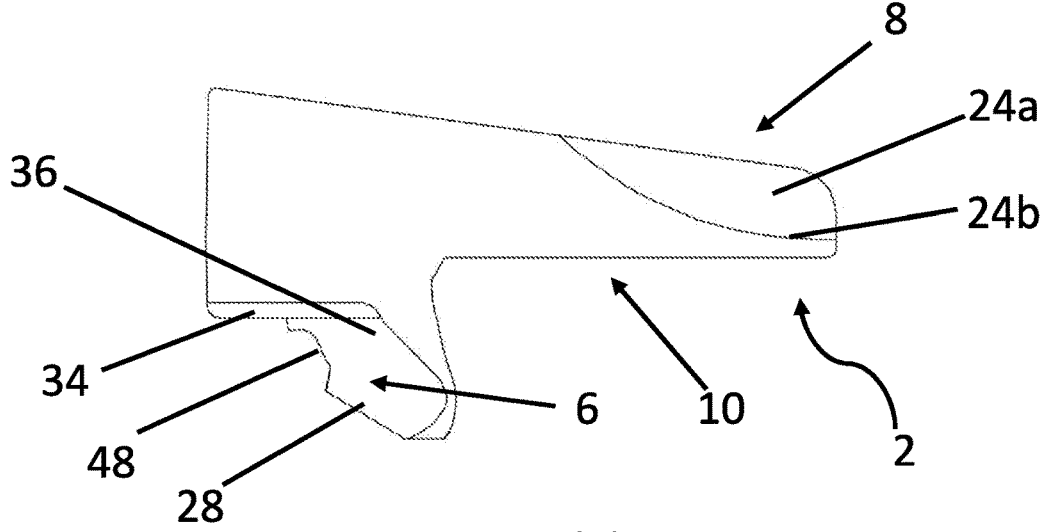
Figure 4C:
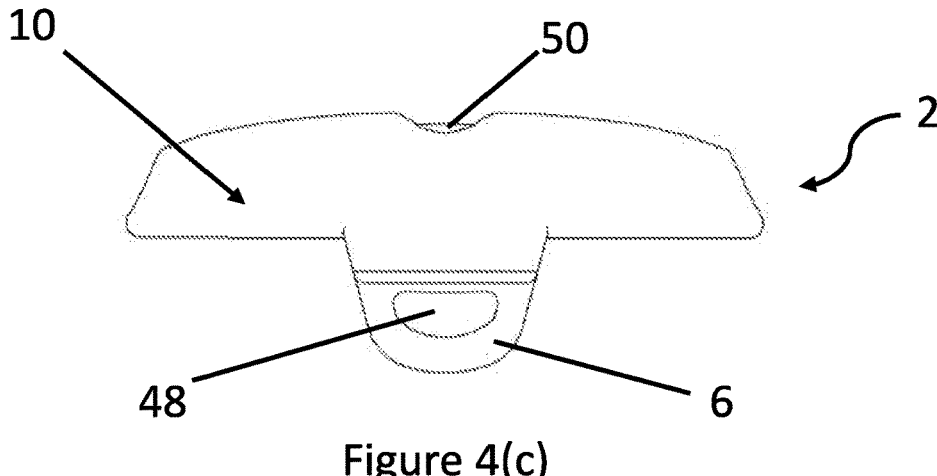

The biteable surface 34 of the step 32 (see FIGS. 1 and 4(b)) is configured to receive or abut the wearer's lower front teeth if they attempt to bite their teeth together. This region 34 may be formed from a softer material such that biting into does not damage the wearer's teeth. In the depicted embodiment, the biteable region is in the form of a planar surface 34 provided at a base 36 of the sloped guide 6. For example, referring to FIG. 2(b), the outer component 10 may be provided with circular openings 38 and/or a slot 40 via for retaining the pliable biteable material 34.

Figure 3A:
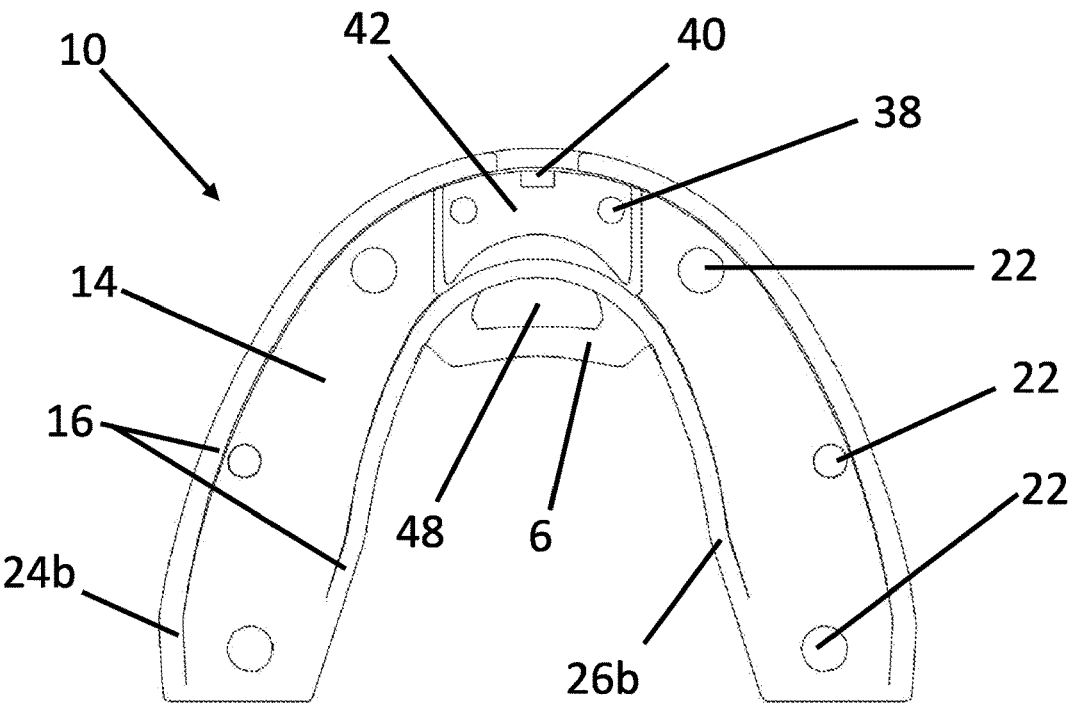
FIG. 3(*a*) is a top view of the outer component of FIG. 2(*b*)

FIG. 3(a) shows a top view of the outer shell component 10. An interior 42 of the downwardly extending step 32 is substantially hollow and is configured to receive a complementary projecting foot 44 formed at a central front region of the inner component 8. The foot 44 may plug directly into the hollow 42 of the step 32 from above, thereby providing further interlocking of the two components 8, 10 together.

In embodiments of the invention, the front central region of the inner component 8, such as the projecting foot 44 thereof, may comprise a planar region 46 formed from a pliable or mouldable putty-like material, which can be pressed firmly into the hollow 42 of the step 32. As pressure is applied, the pliable material 46 can exude through the openings 38 and slot 40 of the outer component 10, and then be moulded to form a soft biteable plane 34, as shown in FIG. 1.

In embodiments of the mouthguard 2, the guide 6 is also provided with a central through-hole or opening 48 through which air can flow into the wearer's mouth. As such, even if the wearer's mouth is substantially closed and their lower front teeth are in contact with the biteable platform region 34, their breathing will not be obstructed by the mouthguard 2 or the guide 6 thereof since air can still travel unobstructed through the opening 48 in the guide 6.

In embodiments of the mouthguard 2, an upper central portion of the mouthguard 2 may be formed with a slightly curved depression 50 to make room for the wearer's superior labial frenulum. In the depicted embodiment, a groove 50 is formed at a central front region of both the inner component 8 and the outer component 10 of the mouthguard 2.

Many modifications of the above embodiments will be apparent to those skilled in the art without departing from the scope of the present invention. For example, the mouthguard 2 can be any range of sizes, widths and lengths to suit the needs of the wearer.

In embodiments of the mouthguard 2, the position and/or extension of the guide 6 may be adjustable. For example, the guide 6 may be adjustably and movably secured or attached to the outer component 10. From the perspective of the wearer, the guide 6 may thus be moved forward or rearward to better suit the configuration of the wearer's jaws. The guide 6 could also be configured such that an angle thereof is adjustable so that it can be tilted forward or rearward to better suit the wearer's jaws.

It is envisaged that the extent to which the guide 6 and/or platform 32 protrudes downwardly may also be adjusted. For example, the guide 6 and/or platform 32 may be extended or adjusted downwardly in the direction of the wearer's lower jaw to increase the spacing between the wearer's front teeth when they bite against the platform 32.

It is also envisaged that the mouthguard 2 can be worn over the lower teeth, wherein the guide 6 extends upwardly but abuts against the upper teeth in such a way as to also bring the lower jaw downwards and forwards as the wearer closes their teeth together.

The mouthguard need 2 not have the biteable platform region 32, and the guide 6 does not need an airflow opening 48. The guide 6 itself need not have a curved profile, and may instead simply be a relatively flat tab-like protrusion that is angled rearwardly from the perspective of the wearer.

In certain embodiments, the mouthguard 2 may not necessarily require two separate components 8, 10. For example, it is envisaged that wearing the outer component 10 could protect against bruxism and may help alleviate issues such as TMJ dysfunction and snoring. In such an embodiment, the channel 14 of the mouthguard 2 may be formed from a relatively soft material to be more comfortable against the wearer's teeth and gums.

In the depicted embodiments, the channel of the mouthguard (e.g. the channels 4, 14 of the inner and outer components 8, 10, respectively) are, in part, defined by opposed walls 12, 16 which are substantially continuous. However, these walls 12, 16 need not be continuous and may have openings or breaks to reduce the surface area of the mouthguard 2 that is in contact with the user's gums and/or teeth. The height of the sidewalls 12, 16 of the mouthguard 2 may extend to contact or even cover some of the wearer's gums, however in other embodiments the sidewalls 12, 16 may not contact the gums at all.

In certain embodiments of the mouthguard 2, an interior surface of the inner component 8, such as an inner face of one of its opposed sidewalls 12, may comprise one or more grooves or ridges that help a user better locate their teeth in the inner component 8. For example, a substantially vertical and slightly raised ridge may protrude from a central front interior face of the inner component 8 which is configured to locate at a gap between the wearer's top front two teeth.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A mouthguard for protecting a wearer's teeth from bruxism, the mouthguard comprising:

an inner component comprising a U-shaped channel configured to receive at least a portion of a first row of teeth of the wearer;

an outer component comprising:

a rigid outer shell comprising a U-shaped channel, and a guide configured to extend towards the wearer's second row of teeth, the guide being configured to guide the jaw of the second row of teeth forwards and downwards in the same motion, such that in use, when the wearer brings their teeth together, front teeth of the opposed jaws are brought into alignment with one another; and

a bite region at a base of the guide configured, in use, to abut the front teeth of the second row of teeth when the wearer brings their teeth together; and wherein the U-shaped channel of the outer component is configured to receive the inner component, wherein the U-shaped channel of the inner component fits into the U-shaped channel of the outer component; and wherein the bite region comprises:

(a) an at least partially hollow step disposed between the the U-shaped channel of the inner component and the guide, which step comprises one or more openings; and (b) pliable foot extending downwardly from an interior portion of the inner component and being insertable into the at least partially hollow step and exudable through the one or more openings of the step so as to define a surface of the bite region for abutment against the wearer's teeth.

2. The mouthguard of claim 1, wherein the bite region is spaced from the U-shaped channel of the outer component, such that in use, when the wearer bites against the bite region, the bite region maintains the front teeth of the opposed jaws at a distance from one another.

3. The mouthguard of claim 1, configured to be worn at least partially over the wearer's top row of teeth, the guide comprising a ramped surface which extends rearwardly and downwardly towards the wearer's bottom row of teeth such that, in use, as the wearer attempts to bring their rows of teeth together, front teeth of the wearer's bottom row of teeth contact a lower end of the guide and are guided forward and downwards in the same motion, so as to be aligned and spaced apart from the front teeth of the wearer's top row of teeth.

4. The mouthguard of claim 1, wherein the guide comprises an opening through which air can flow.

5. The mouthguard of claim 1, wherein the interior portion is mouldable and comprises said U-shaped channel of the inner component configured to mould to the wearer's teeth.

6. The mouthguard of claim 1, further comprising one or more grooves or ridges configured to locate the wearer's teeth in the mouthguard.

* * * * *